United States Patent
Jakab et al.

(10) Patent No.: US 10,765,489 B2
(45) Date of Patent: Sep. 8, 2020

(54) TOOL PLACEMENT MANIPULATOR

(71) Applicants: CANON U.S.A., INC., Melville, NY (US); THE BRIGHAM AND WOMEN'S HOSPITAL INC., Boston, MA (US)

(72) Inventors: Peter Denes Jakab, Boston, MA (US); Nobuhiko Hata, Newton, MA (US); Takahisa Kato, Brookline, MA (US); Peter Tia, Dracut, MA (US)

(73) Assignees: Canon U.S.A., Inc., Melville, NY (US); The Brigham and Women's Hospital Inc., Boston, MA (US)

( * ) Notice: Subject to any disclaimer, the term of this patent is extended or adjusted under 35 U.S.C. 154(b) by 265 days.

(21) Appl. No.: 16/071,051

(22) PCT Filed: Jan. 27, 2017

(86) PCT No.: PCT/US2017/015328
§ 371 (c)(1),
(2) Date: Jul. 18, 2018

(87) PCT Pub. No.: WO2017/132505
PCT Pub. Date: Aug. 3, 2017

(65) Prior Publication Data
US 2020/0078130 A1 Mar. 12, 2020

Related U.S. Application Data

(60) Provisional application No. 62/288,927, filed on Jan. 29, 2016.

(51) Int. Cl.
*A61B 90/11* (2016.01)
*A61B 34/30* (2016.01)
(Continued)

(52) U.S. Cl.
CPC .............. *A61B 90/11* (2016.02); *A61B 34/30* (2016.02); *A61B 2017/00853* (2013.01);
(Continued)

(58) Field of Classification Search
CPC ............ A61B 90/11; A61B 2017/3407; A61B 2017/3409; A61B 90/10; A61B 2090/103;
(Continued)

(56) References Cited

U.S. PATENT DOCUMENTS 4,841,967 A 6/1989 Chang et al.
4,883,053 A 11/1989 Simon
(Continued)

FOREIGN PATENT DOCUMENTS

CA 2784988 A1 2/2013
EP 2193750 A1 6/2010
(Continued)

OTHER PUBLICATIONS

Fischer, G. S., et al. (2006). "MRI Guided Needle Insertion—Comparison of Four Technique" In Annual Scientific Conference of the Society of Interventional Radiology. (Abstract only).
(Continued)

*Primary Examiner* — Katrina M Stransky
(74) *Attorney, Agent, or Firm* — Canon U.S.A., Inc., IP Division

(57) ABSTRACT

Exemplary relates to medical devices and in particular to a tool placement manipulator with multiple rotary guides and rotation bodies, the rotation bodies being free rotationally to the ring shaped rotary guides and rotational axis of the first rotary guide being slanted with respect to the rotational axis of the second rotary guide. The tool placement manipulator has at least one socket and at least one transmission element that transmits torques from the socket to rotation bodies.

18 Claims, 5 Drawing Sheets

(51) Int. Cl.
*A61B 17/00* (2006.01)
*A61B 17/34* (2006.01)
(52) U.S. Cl.
CPC .............. *A61B 2017/00951* (2013.01); *A61B 2017/3407* (2013.01); *A61B 2017/3409* (2013.01)
(58) Field of Classification Search
CPC ... A61B 2090/101; A61B 90/13; A61B 90/14; A61B 2034/304; A61B 17/3403; A61B 2017/3405
See application file for complete search history.

(56) References Cited

U.S. PATENT DOCUMENTS

| | | | |
|---|---|---|---|
| 4,919,382 A * | 4/1990 | Forman | B25J 17/0266 248/178.1 |
| 4,955,891 A | 9/1990 | Carol | |
| 5,196,019 A | 3/1993 | Davis et al. | |
| 5,201,742 A | 4/1993 | Hasson | |
| 5,280,427 A | 1/1994 | Magnusson et al. | |
| 5,682,892 A | 11/1997 | Selder et al. | |
| 5,706,812 A | 1/1998 | Strenk et al. | |
| 5,957,934 A | 9/1999 | Rapoport | |
| 5,993,463 A | 11/1999 | Truwit | |
| 6,079,681 A | 6/2000 | Stern et al. | |
| 6,119,032 A | 9/2000 | Martin et al. | |
| 6,185,445 B1 | 2/2001 | Knuttel | |
| 6,529,764 B1 | 5/2003 | Kato et al. | |
| 6,676,669 B2 | 1/2004 | Charles et al. | |
| 6,966,876 B2 | 11/2005 | Irion et al. | |
| 7,083,608 B2 | 8/2006 | Tomita et al. | |
| 7,187,104 B2 | 3/2007 | Yamamoto et al. | |
| 7,379,769 B2 | 5/2008 | Piron et al. | |
| 7,636,596 B2 | 12/2009 | Solar | |
| 7,803,164 B2 | 9/2010 | Gielen et al. | |
| 7,824,417 B2 | 11/2010 | Magnusson et al. | |
| 7,892,243 B2 | 2/2011 | Stuart | |
| 8,241,301 B2 | 8/2012 | Zhang et al. | |
| 8,308,740 B2 | 11/2012 | Tolley et al. | |
| 9,125,676 B2 | 9/2015 | Sahni | |
| 9,222,996 B2 | 12/2015 | Fujimoto et al. | |
| 2001/0000940 A1 | 5/2001 | Maruyama et al. | |
| 2002/0019641 A1 | 2/2002 | Truwit | |
| 2003/0078502 A1 | 4/2003 | Miyaki | |
| 2003/0107299 A1 | 6/2003 | Fujimoto et al. | |
| 2004/0064148 A1 | 4/2004 | Daum et al. | |
| 2005/0216026 A1 | 9/2005 | Culbert | |
| 2005/0261581 A1 | 11/2005 | Hughes et al. | |
| 2006/0149147 A1 | 7/2006 | Yanof | |
| 2006/0229641 A1* | 10/2006 | Gupta | A61B 17/3403 606/130 |
| 2007/0191867 A1 | 8/2007 | Mazzocchi | |
| 2007/0276407 A1 | 11/2007 | Vogele | |
| 2008/0004481 A1 | 1/2008 | Bax | |
| 2008/0009743 A1 | 1/2008 | Hayaska | |
| 2008/0033356 A1 | 2/2008 | Kluge et al. | |
| 2008/0161829 A1 | 7/2008 | Kang | |
| 2008/0167663 A1 | 7/2008 | De Mathelin et al. | |
| 2008/0200928 A1* | 8/2008 | Savall Calvo | A61B 90/50 606/130 |
| 2009/0018390 A1 | 1/2009 | Honda et al. | |
| 2009/0079431 A1 | 3/2009 | Piferi et al. | |
| 2009/0234369 A1 | 9/2009 | Bax et al. | |
| 2010/0010505 A1 | 1/2010 | Herlihy et al. | |
| 2010/0082040 A1 | 4/2010 | Sahni | |
| 2010/0168766 A1 | 7/2010 | Zeng et al. | |
| 2011/0126844 A1 | 6/2011 | Cinquin et al. | |
| 2011/0190787 A1 | 8/2011 | Sahni | |
| 2011/0237881 A1 | 9/2011 | Kunz | |
| 2011/0251624 A1 | 10/2011 | Yi et al. | |
| 2012/0022368 A1 | 1/2012 | Brabrand et al. | |
| 2012/0143048 A1 | 6/2012 | Finlay | |
| 2013/0069651 A1 | 3/2013 | Luminani | |
| 2013/0267834 A1 | 10/2013 | McGee | |
| 2013/0345718 A1 | 12/2013 | Crawford | |
| 2014/0018822 A1 | 1/2014 | Main | |
| 2014/0052154 A1 | 2/2014 | Griffiths et al. | |
| 2014/0121675 A1 | 5/2014 | Bax | |
| 2014/0128881 A1 | 5/2014 | Tyc et al. | |
| 2014/0128883 A1 | 5/2014 | Piron et al. | |
| 2014/0200445 A1 | 7/2014 | Boezaart | |
| 2014/0275978 A1 | 9/2014 | Fujimoto et al. | |
| 2014/0275979 A1 | 9/2014 | Fujimoto et al. | |
| 2014/0336670 A1 | 11/2014 | Brabrand et al. | |
| 2014/0350572 A1 | 11/2014 | Elhawary et al. | |
| 2015/0238266 A1 | 8/2015 | Fujimoto et al. | |
| 2016/0074063 A1 | 3/2016 | Arimitsu et al. | |
| 2017/0014200 A1 | 1/2017 | Onuma et al. | |
| 2017/0030557 A1 | 2/2017 | Chen et al. | |
| 2017/0071626 A1 | 3/2017 | Onuma et al. | |
| 2017/0258489 A1 | 9/2017 | Galili et al. | |

FOREIGN PATENT DOCUMENTS

| | | |
|---|---|---|
| EP | 2561821 A1 | 2/2013 |
| JP | H10-502566 A | 3/1998 |
| JP | H11-155880 A | 6/1999 |
| JP | 2001-104279 A | 4/2001 |
| JP | 2004320846 A | 11/2004 |
| JP | 2005083961 A | 3/2005 |
| JP | 2008-528197 A | 7/2008 |
| JP | 2008237971 A | 10/2008 |
| JP | 2009-539509 A | 11/2009 |
| WO | 2011082517 A1 | 7/2011 |
| WO | 2011146018 A1 | 11/2011 |
| WO | 2012178109 A1 | 12/2012 |
| WO | 2013084107 A2 | 6/2013 |
| WO | 2014152685 A1 | 9/2014 |

OTHER PUBLICATIONS

Koethe Yilun et al., MAXIO "Accuracy and effaicacy of percutaneous biopsy and ablation using robotic assistance under computed tomography guidance: a phantom study" Eur Radiol 2013.
Maxio Brochure: Planning and Targeting for CT guided Procedures by Perfint.
Palmer et al. "Develoment and Evaluation of optical needle depth sensor for percutaneous diagnosis and therapies" Medical Imaging 2014 Proc. of SPIE vol. 9036, 90362M.
Perfint, Inc Maxio Robot—Features http://www.perfinthealthcare.com/MaxioFeatures.asp Accessed Sep. 11, 2015.
Song et al., Biopsy Needle Artifact Localization in MRI-guided Robotic Transrectal Prostate Intervention, IEEE transactions on Biomedical Engineering,Jul. 2012.
Song, S.E., et al., "Design Evaluation of a Double Ring RCM Mechanism for Robotic Needle Guidance in MRI-guided Liver Interventions", International Conference on Intelligent Robots and Systems, Nov. 3-7, 2013, Tokyo, Japan.
Hata et al.,"MRI-Compatible Manipulator With Remote-Center-of-Motion Control", Department of Radiology, Brigham and Women's Hospital, and Harvard Medical School, Boston; Center for Clinical Investigation, Brigham and Women's Hospital and Harvard Medical School, Boston; Biomedical MR Science Center, Shiga University of Medical Science, Shiga, May 2008, http://www.ncbi.nlm.nih.gov/pmc/articles/PMC2815332/.
Stoianovici, D., et al, "Endocavity Ultrasound Probe Manipulators", IEEE/ASME Transactions on Mechatronics, Jun. 2013, pp. 914-921, vol. 18, No. 3.

* cited by examiner

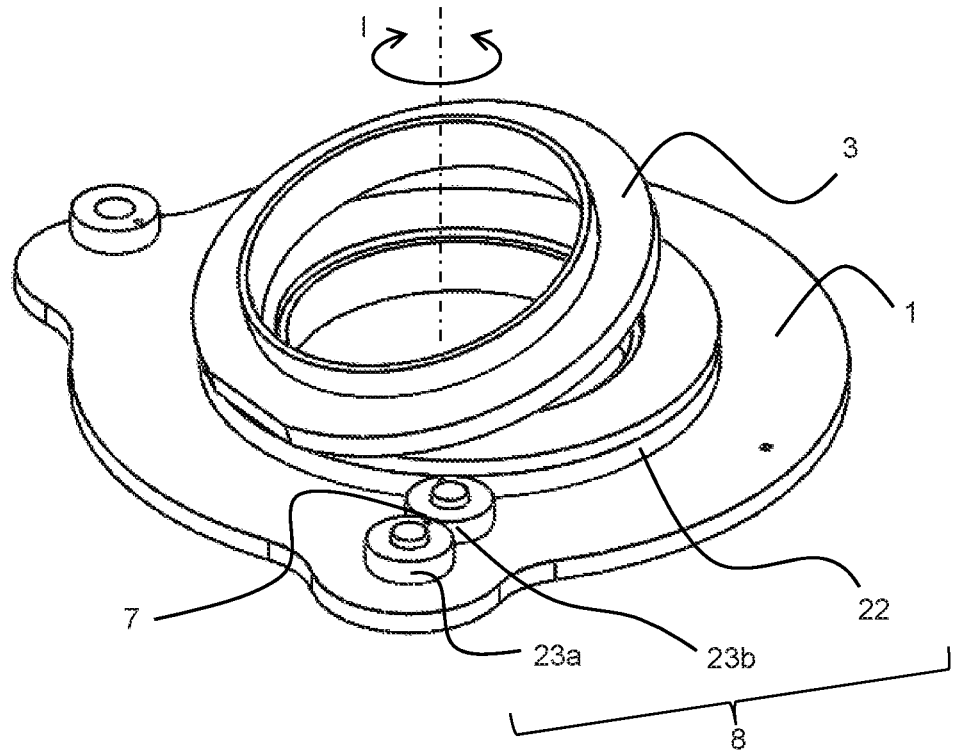

TOOL PLACEMENT MANIPULATOR

CROSS-REFERENCE TO RELATED APPLICATION(S)

This application claims priority to U.S. Provisional Application Ser. No. 62/288,927 filed 29 Jan. 2016, the content of which is incorporated herein by reference in its entirety.

FIELD OF THE DISCLOSURE

The present disclosure generally relates to medical devices and in particular to a tool placement manipulator with two rotary guides.

BACKGROUND INFORMATION

The accurate and precise placement of a needle-like instrument according to plan based on medical images, such as computed tomography (CT) and Magnetic Resonance Imaging (MRI), is critical in percutaneous interventions. To reduce placement error of the instruments and user dependency, different systems have been disclosed.

EP 2561821 discloses a tool placement manipulator that supplies a physical guidance, i.e. a needle holder, to the planned orientation with the planned skin entry point. Physicians create needle trajectory plans by using medical images of the patient. The manipulator including a robotic arm is mounted on a floor near to a medical imaging machine. The manipulator is associated with a movable patient bed of the medical imaging machine and locates the physical guidance to the target position/orientation by calculating command to the robotic arm.

U.S. Pat. Pub. 2007/0276407 discloses another tool placement manipulator that supplies physical guidance. The manipulator is mounted on the patient bed and directs the physical guidance to the target. These systems are fixed with respect to a coordinate system of the bed or the medical imaging machine. Therefore, the position accuracy or precision are sensitive to the patient dislocation. Moreover, the subsystem that supplies the physical guidance tends to become bulky since this subsystem needs to include a mounting part from the floor or the bed and thus potentially hampers physicians' line of flow in interventions.

To improve this issue, different systems have been disclosed. For example, U.S. Pat. Pub. 2006/0229641 provides a patient-mount tool placement manipulator. The subsystem that supplies the physical guidance is mounted on a patient skin. Placing the subsystem on the patient skin can decrease the sensitivity of the position accuracy or precision to the patient dislocation. Also since this subsystem does not involve the mounting part from the floor, the bed or the ceiling, the subsystem can have less chance to encumber the physicians' line of the flow in the interventions. However, this system is still limited. The tool placement manipulator in this publication does not have an opening to an insertion point of a patient's skin from natural line of physicians' sight. So physicians have to involve limitations to see and to touch the insertion point with this system. Moreover, the manipulator includes the motors that are in sockets on the movable arc-shaped parts near to the needle holder. When the motors are mounted on the sockets, the cables of these motors also extend from the sockets to the control part. These motors, the sockets and the cables potentially hamper physicians' line of flow in interventions.

A solution to these issues was provided in U.S. Pat. No. 9,222,996, herein incorporated by reference in its entirety. A system having two ring shaped rotary guides, where the second ring shaped rotary guide is slanted with respect to the first ring shaped rotary guide. Motorized actuators, that include piezoelectric actuators, rotary sliders, and ultrasonic motors, as well as simply manually rotating the first and second rotary guides. However, the cost of the motorized actuators can be high, and does not aid in creating a device that can be sterilized.

Thus, there is need for a tool placement manipulator that overcomes the deficiencies as described herein.

SUMMARY OF EXEMPLARY EMBODIMENTS

According to at least one embodiment of the invention, there is provided a tool placement manipulator comprising: a first ring shaped rotary guide; a first rotation body which is fixed and is free rotationally to said first ring shaped rotary guide; a second ring shaped rotary guide attached to the first rotation body, the second ring shaped rotary guide being movable along with the first rotation body; a second rotation body which is fixed and is free rotationally to said second ring shaped rotary guide; a third ring shaped rotary guide attached to either the first ring shaped rotary guide or the first rotation body; a third rotation body which is fixed and is free rotationally to the third ring shaped rotary guide; a tool holder which is fixed to the second rotation body and is configured for holding a tool along an axis, the tool holder being movable along with the second rotation body; wherein a rotational axis of the first rotary guide and a rotational axis of the second rotary guide are slanted with respect to each other, and wherein the rotational axis of the first rotary guide, the rotational axis of the second rotary guide, and the tool holder axis cross each other at one point, at least one socket attached to the first ring shaped rotary guide; at least one transmission element which is connected between said socket and the first or the third rotation body, and transmits torques from the at least one socket to the first and the third rotation bodies; wherein the third rotation body connects to the second rotation body and transmits the torques to the second rotation body.

In some embodiments, the third rotation body can include an upper spur gear that is engaged with one of the transmissions and shares the rotational axis of the first rotary guide, and a bevel gear that is fixed to the upper spur gear and shares the rotational axis of the first rotary guide, and the second rotation body can include a bevel pinion that is engaged with the bevel gear and shares the rotational axis of the second rotary guide. In yet other embodiments, the first rotation body includes a bottom spur gear that is engaged with one of the transmissions and shares the rotational axis of the first rotary guide.

In some embodiments, the tool placement manipulator also includes: a first socket which is fixed to the first ring shaped rotary guide; a first transmission element which is connected between said first socket and the first rotation body and transmits torques from the at least one socket to the first rotation body; a second socket which is fixed to the first ring shaped rotary guide; a second transmission element which is connected between said second socket and the third rotation body. Torque is transmitted from a motor to the third rotation body; wherein the third rotation body connects to the second rotation body and transmits the torques to the second rotation body. In other embodiments, the tool placement manipulator also includes two nobs or two motors that independently control the two transmission elements.

In some embodiments, the tool placement manipulator also includes: a first socket fixed to the first ring shaped rotary guide; a first transmission element which is connected between said first socket and the first rotation body. Torque is transmitted from a first motor to the first rotation body; wherein the transmission transmits torques from the first motor to the third rotation body and the third rotation body connects to the second rotation body and transmits the torques to the second rotation body.

In yet other embodiments, the socket is located on the same side of the first rotary shaped guide as the side of the first rotation body, or the stopper(s) are attached to the socket that is configured to stop the motion of the transmission with a physicians' operation. There may be a first socket and a second socket, and the at least one transmission may comprise a first transmission and a second transmission, wherein the second socket and the second transmission have the same function as the first socket and the first transmission, respectively. In some embodiments, the tool placement manipulator is configured such that the first socket accepts the motor and the second socket accepts a stopper attached to the second socket that is configured to stop the motion of the transmission with a physician's operation.

In some embodiments, the first transmission transmits torques to the first and the second rotation bodies have different transmission ratio. In some embodiments, the gears and/or pinions are made of self-lubricating plastics. In some embodiments the tool placement manipulator includes an adhesive located on the first ring shaped rotary guide. This embodiment provides for a simple means of attaching the manipulator onto a patient. The tool placement manipulator may be designed for a single use and may be designed for a specific patient. The tool holder may be configured for holding a single needle or multiple needles (either simultaneously or sequentially).

In some embodiments there is provided a manipulator comprising: a first ring shaped rotary guide; a first rotation body which is fixed and is free rotationally to said first ring shaped rotary guide; a second ring shaped rotary guide attached to the first rotation body, the second ring shaped rotary guide being movable along with the first rotation body; a second rotation body which is fixed and is free rotationally to said second ring shaped rotary guide; a third ring shaped rotary guide attached to either the first ring shaped rotary guide or the first rotation body; a third rotation body which is fixed and is free rotationally to the third ring shaped rotary guide; at least one socket attached to the first ring shaped rotary guide; and at least one transmission element which is connected between said socket and the first or the third rotation body, and transmits torques from the at least one socket to the first and the third rotation bodies; and wherein the third rotation body connects to the second rotation body and transmits the torques to the second rotation body.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIG. 9 is a schematic view of a tool placement manipulator.

Figure 1:
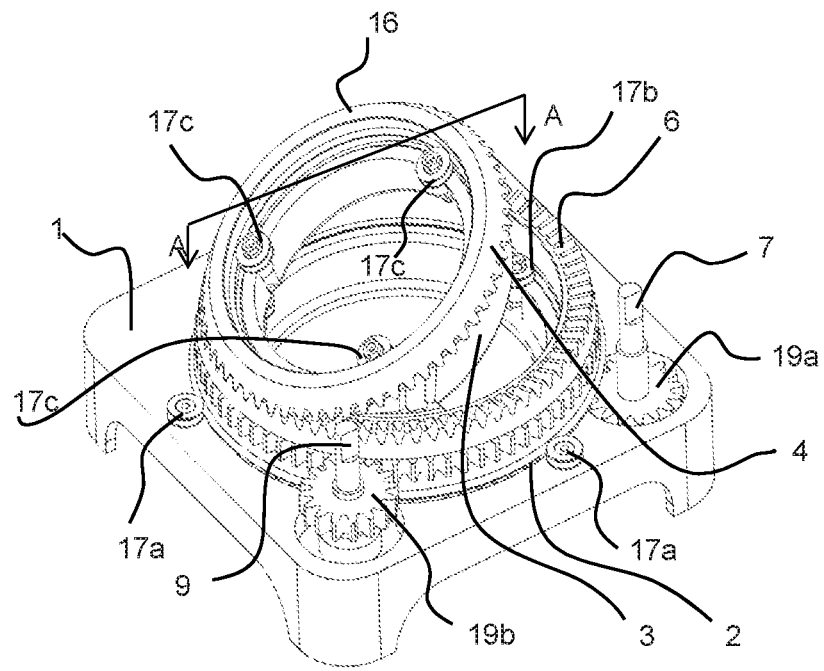
FIG. 1 is an illustration of an exemplary tool placement manipulator to a first embodiment of the present invention.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

The embodiments are based on the object of providing a tool placement manipulator and method of use that accurately and precisely places a tool for percutaneous intervention. This tool placement manipulator has at least two ring shaped rotary guides that are connected to rotational bodies, in which torque may be applied via at transmission element. This tool placement manipulator does not require direct manual rotation of the rings and does not require a motor located on the ring.

Embodiment 1

A first embodiment of an exemplary tool placement manipulator will now be described with reference to FIGS. 1 to 6. FIG. 1 shows a trimetric projection of the tool placement manipulator The tool placement manipulator comprises a first ring shaped rotary guide 1, two series of gear transmission lines with two first and second sockets 7 and 9 and tool holder interface 16 to mount a tool holder (e.g., a needle holder that guide needle-like device). First ring shaped rotary guide 1 is fixed a bottom surface, particularly which is a patient skin in this embodiment.

A first rotational body 2 is mounted on first ring shaped rotary guide 1 with bearings 17a and is configured and adapted to rotate freely. The first rotation body 2 is connected to a second ring shaped rotary guide 3 which, in this embodiment, is shown slanted relative to the first rotation body 2 and rotate with first rotation body 2. A second rotational body 4 is concentric with and is fixed on second ring shaped rotary guide 3 with bearings 17c and is configured and adapted to rotate freely. A third ring shaped rotary guide 5 is embedded on first rotation body 2 and a third rotation body 6 is mounted with bearings 17b and is configured and adapted to rotate freely.

Figure 2:
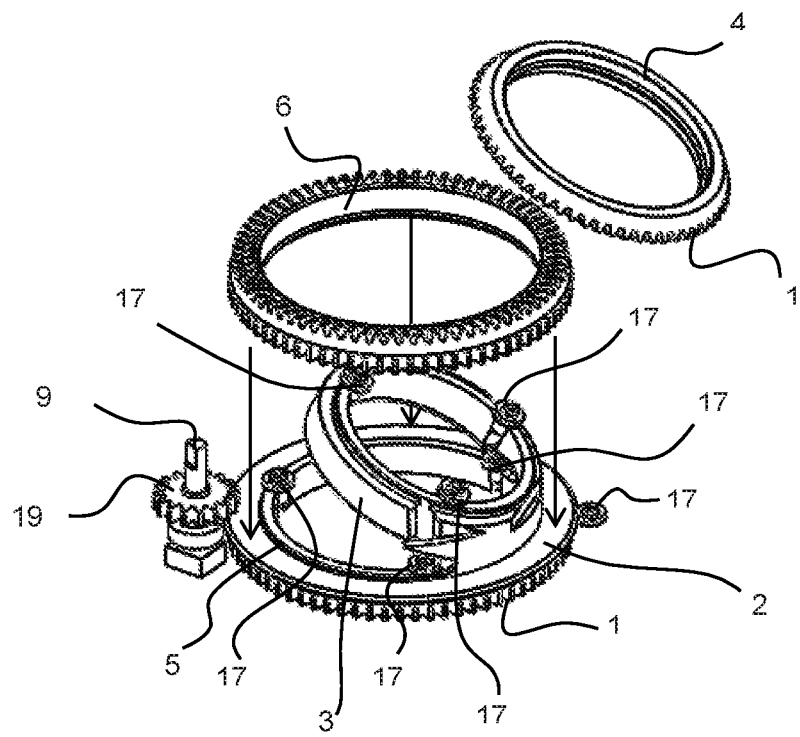
FIG. 2 shows an exploded view of the tool placement manipulator in FIG. 1.
Figure 3:
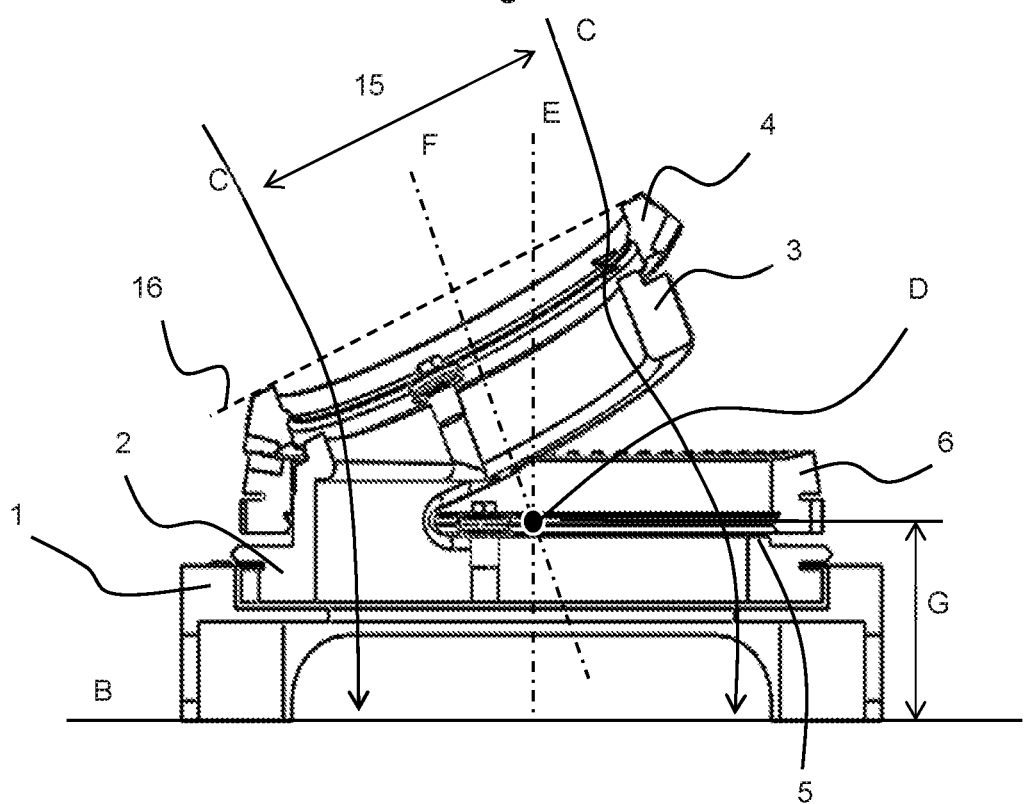
FIG. 3 depicts a cross sectional view on line A-A in FIG. 1.

FIGS. 2 and 3 further illustrate the tool placement manipulator in FIG. 1. The gear transmission lines comprise three rotation bodies; first rotation body 2, second rotation body 4 and third rotation body 6. These rotation bodies are mounted on rotary guides and include gears as follow. The tool placement manipulator is mounted on surface B. In this embodiment, surface B is a skin surface of a patient. Two curves C in FIG. 3 signify range of opening 15 and shows accessible direction by physicians as arrows. The opening 15 provides windows to access the patient skin from the needle holder side.

First ring shaped rotary guide 1 locates on surface B and is mechanically grounded on surface B. The ring shaped rotary guide 1 may be directly adhered (e.g., via s strap or sterile tape) to the surface which may be a patient's skin. Alternatively, it may be mounted on a separate element which is adhered or otherwise mounted onto the surface. For example, a coil may be located below the ring shaped rotary guide 1 for use in a MRI. First rotation body 2 is mounted on first ring shaped rotary guide 1 with bearings 17a and is rotatable freely to first ring shaped rotary guide 1 along axis E in FIG. 3. Also, first rotation body 2 is connected to second ring shaped rotary guide 3. Second ring shaped rotary guide 3 is slanted to first rotation body 2 and rotate with first rotation body 2 along axis E.

Figure 5:
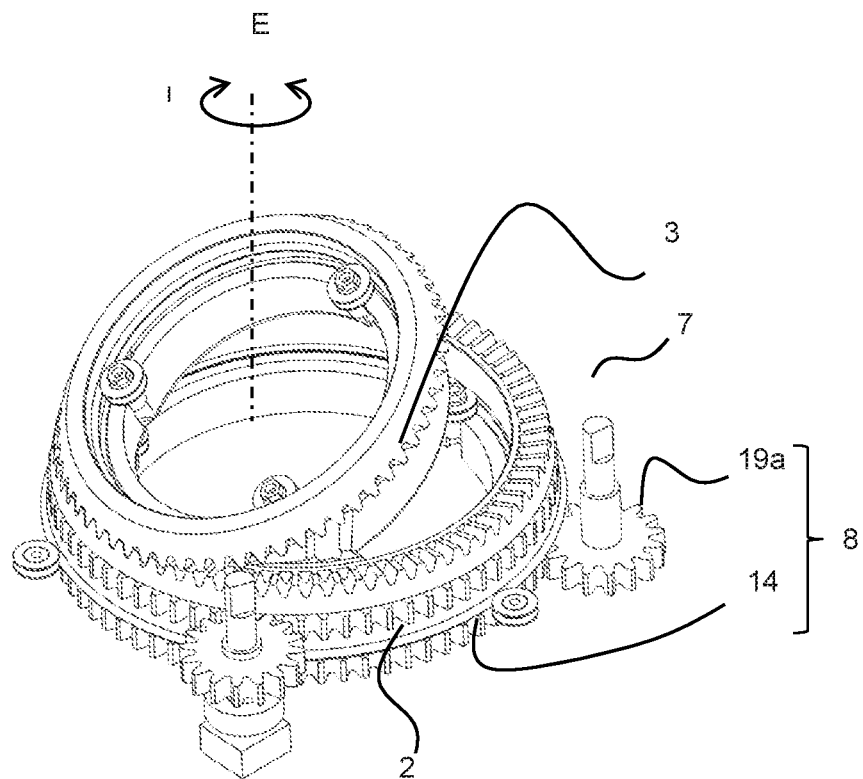
FIG. 5 illustrates the rotation of the tool placement manipulator in FIG. 1 rotating around axis E.

First rotation body 2 includes bottom spur gear 14 and makes first transmission 8 with engagement with spur pinion 19a. An input torque is applied to first socket 7, which is connected to spur pinion 19a with shaft, first socket 7 transmits through spur pinion 19a, bottom spur gear 14 and creates revolution I of second ring shaped rotary guide 3 along axis E (FIG. 5). The input torque can be generated by variety of methods.

In one implementation, a nob, which is not shown in FIG. 5, can be attached on or in first socket 7, since the first socket 7 can fix the nob around the rotation axis of the first socket 7 with a key feature. The nob, or similarly some other element to facilitate rotation of the socket, can be rotated by physician's hands and put the input torque to first socket 7. To show a target rotation, the first socket 7 can have numerical guides to indicate rotate angle and turning number. With the numerical guides, the physician can turn the nob to a target rotation. Also, the nob can be detachable after targeting the first socket 7. By detaching the nobs, the physician can avoid turning the first socket 7 mistakenly.

Moreover, in some embodiments, the socket can provide clicking feeling or sound to the physicians for intuitive operation to know rotation of the nobs and for physical reference of the rotation. For example, the socket may provide, e.g., 12 or 18 or 24 reference points in the rotation so that the physician will know that they have rotated the nob, e.g., 30°, 20°, 15°for each click. This can be useful for manual control of the tool placement manipulator rotation. In some exemplary implementations, the rotation angles are calculated as discussed herein below and are provided to the physician as simply as how much to rotate each nob.

In the other implementation, a first motor, which is also not shown in FIG. 5, can be attached on first socket 7. A moving part of the motor can be fixed with the same principal as for the nobs. Also, a stationary part of the motor is mounted on first ring rotatory shape guide 1. The motor rotates first socket 7 with appropriate control command to target. The motor may be, for example, attached via a drive shaft such that the motor is located either proximal to the socket or away from the socket (e.g., outside the sterile field during a surgical operation).

In the other implementation, a first motor, which is also not shown in FIG. 5, can be attached on first socket 7. A moving part of the motor can be fixed with the same principal as for the nobs. Also, a stationary part of the motor is mounted on first ring rotatory shape guide 1. The motor rotates first socket 7 with appropriate control command to target. The motor may be, for example, attached via a drive shaft such that the motor is located either proximal to the socket or away from the socket (e.g., outside the sterile field during a surgical operation).

This motor can also be detached from socket 7. This detachable feature of motors can enable to separate expensive reusable part, i.e. the motors from disposable part, i.e. the tool placement manipulator. When the tool placement manipulator are sterile part for surgery, the motor can be attached and detached with a sterilized base to surround the motors. Other divisions of sterile versus non-sterile parts are also contemplated.

As explained above, first socket 7 can accept variety of torque generators to generate the input torque with mechanical interfaces. Though the mechanical interfaces are male key feature in this embodiment, the appropriate different design can be applicable. For example, the nob contains a male component that is position in a female first socket 7. In other embodiments, the socket may comprise a male feature and the nob may contain a female feature. Further, when the tool placement manipulator is connected to a motor, the motor shaft or other means of connection may have either a male or female connection to the tool placement manipulator. Other connection methods as known in the art are also contemplated herein.

The second rotation body 4 is fixed on second ring shaped rotary guide 3 with bearings 17c and is rotatable freely to second ring shaped rotary guide 3 along axis F. Second rotation body 4 also includes bevel gear 12.

Third ring shaped rotary guide 5 is embedded on first rotation body 2. On third ring shaped rotary guide 5, third rotation body 6 is mounted with bearings 17b and is rotatable freely along axis E. Since third rotation body 6 can be stacked on first rotation body 2 with this configuration, this embodiment can reduce footprint of the tool placement manipulator. Consequently, the tool placement manipulator can be applied for more topological surface of body parts. Also small footprint can reduce size of sterile field for the tool placement manipulator.

Figure 4:
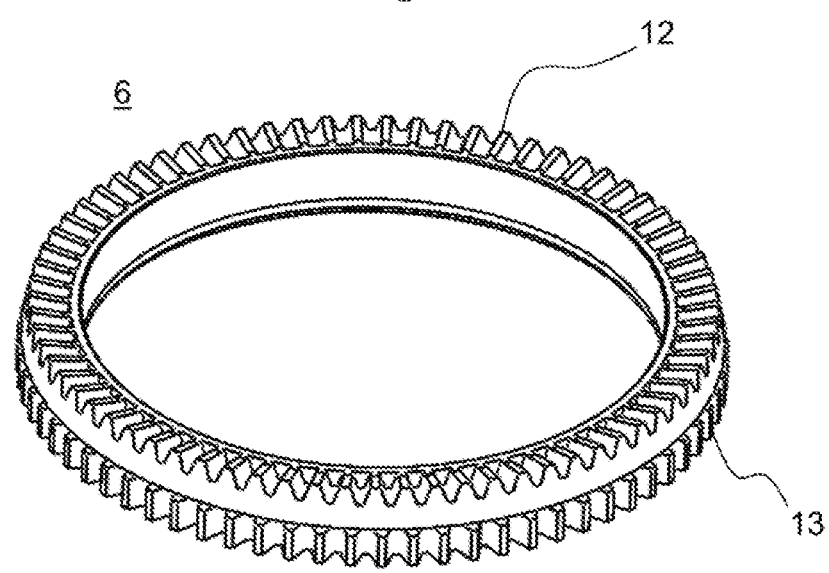
FIG. 4 depicts the third rotation body of FIG. 1.
Figure 6:
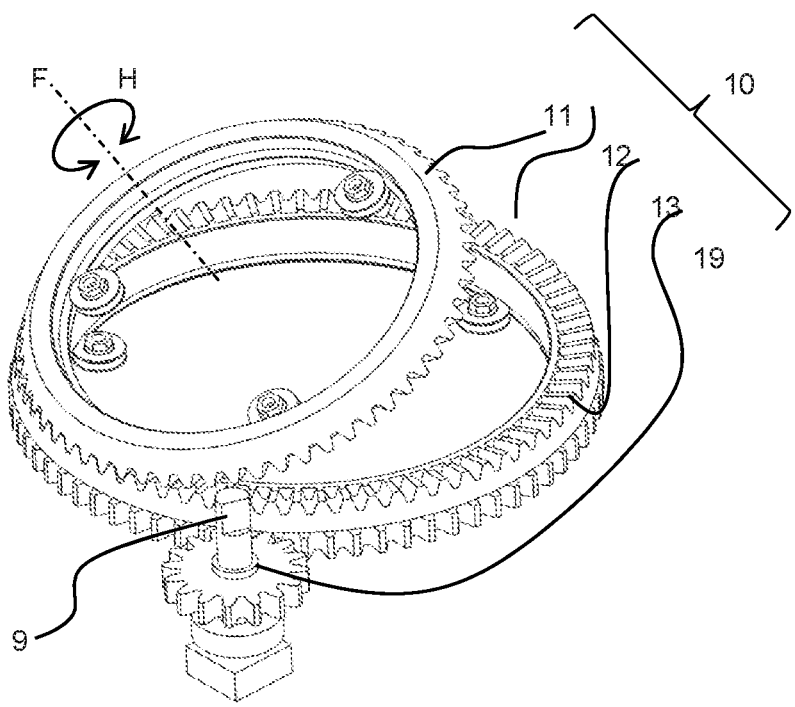
FIG. 6 illustrates the rotation of the tool placement manipulator in FIG. 1 rotating around axis F.

Third rotation body 6 includes bevel pinion 12 and upper spur gear 13 (FIG. 4). Bevel pinion 12 is engaged with bevel gear 11 on second rotation body 4. On the other hand, upper spur gear 13 is engaged with spur pinion 19b (FIG. 6). This gear transmission line with third rotation body 6 makes second transmission 10. With second transmission 10, rotation of second socket 9 can be transmitted into rotation H along axis F (FIG. 6). With this embodiment, the number of teeth on the bevel pinion 12 and on the upper spur gear 13 may are defined separately dependent on the relative size and rotational requirements of the two ring systems.

The second socket 9 can accept variety of torque generators to generate the input torque with mechanical interfaces just like first socket 7. With these two transmission lines, the rotation input from nobs 19a and 19b are transmitted into rotation H along axis F and revolution I along axis E of second rotation body 4. Therefore, the needle holder attached on needle holder interface 16 rotates and revolves along axis E and F. Since axis E and F cross each other at pivot D in FIG. 3, the needle holder moves along remote center of motion (RCM) pivoting at pivot D. RCM models needle targeting maneuver of physicians with two degree of freedom in three dimensional space.

Thus, in some implementations, a nob, which is not shown in FIG. 6 can be attached on in the second socket 9 similar to the nob described herein above. Similar, in some implementation, a second motor, which is not shown in FIG.

6, can be attached on second socket 9. This motor can follow the same principles as described for the first motor. The second motor rotates the second socket 9 with appropriate control command to target.

Pivot D can be located near to a skin entry point of the needle-like medical device. Consequently, the needle holder can target the needle-like medical device based on RCM around the skin entry point that physician planed in advance. In operation, the needle-like medical device is similar to the needle placement manipulator described in U.S. Pat. No. 9,222,996, which shows a first and second ring shaped rotary guides.

Specifically in this embodiment, the tool placement manipulator includes offset G between surface B and pivot D. With offset G, collision of the needle-like medical devices at pivot D can be avoided when the tool placement manipulator guides multiple needle-like medical devices. The first needle-like device can be displaced from pivot D after its insertion when the second needle-like device is inserted. Offset G can be selected with appropriate size for diameter of the needle-like medical device, which is a few times larger than the diameter of the needle-like medical device in this embodiment.

Two rotation angles of first and second sockets 7 and 9 are mapped into two rotation angles of rotation H and revolution I by using the following computation with matrix A:

$$y = Ax \quad (1)$$

where x is as a rotation angle vector for first and second sockets 7 and 9 and y is as a rotation angle vector for rotation H and revolution I. $X=(\theta_{socket\ 7}, \theta_{socket\ 9})^T$, $Y=(\theta H, \theta_I)^T$.

The matrix A is;

$$A = \begin{pmatrix} a & b \\ c & 0 \end{pmatrix} \quad (2)$$

Coefficient a is rotation ratio of $\theta_H$ to $\theta_{socket\ 7}$, Coefficient b is rotation ratio of $\theta_H$ to $\theta_{socket\ 9}$ and coefficient c is rotation ratio of $\theta_I$ to $\theta_{socket\ 7}$. These coefficients can be determined by gear ratios in the tool placement manipulator.

By choosing different rotation ratios of a, b and c, the first and the third rotation bodies 1 and 6 can be rotated different speed with the same rotation speed of first and second sockets 7 and 9. Therefore, one can pick up the rotation ratio for requirement of angular resolution and duration for targeting.

In case of the same rotation ratio between (spur pinion 19a/bottom spur gear 14) and (spur pinion 19b/upper spur gear 13), the same diameter of bottom spur gear 14 and upper spur gear 13 gives identical coefficient a and b. Therefore, with minimal footprint, the computation of mapping between rotations X and Y becomes simple.

Also, to avoid specific combination of gear teeth between pinions and gears, the number of teeth of gears and pinions can be indivisible number each other. With indivisible number of teeth, the different combinations of teeth are engaged through operation of transmissions.

While rotation angle $\theta_H$ is associated with both first and second socket 7 and 9 and 18b, two rotation angles $\theta_H$ and $\theta_I$ can be mapped independently by first and second socket 7 and 9 by using equation (1). Also, with an inverse matrix of matrix A, the target rotation angle of first and second socket 7 and 9 can be calculated from rotation angles $\theta_H$ and $\theta_I$ inversely. The rotation angles $\theta_H$ and $\theta_I$ are determined by the target orientation of the needle holder by using kinematics of the tool placement manipulator of Song. [See Song S, Tokuda J, Tuncali K, Yamada A, Torabi M, Hata N., "Design Evaluation of a Double Ring RCM Mechanism for Robotic Needle Guidance in MRI-guided Liver Interventions", IEEE/RSJ International Conference on Intelligent Robots and Systems (IROS), Nov. 3-7, 2013]. Therefore, the tool placement manipulator can be controlled to the planed target position of the needle holder associated with the rotation angles $\theta_H$ and $\theta_I$.

First and second socket 7 and/or 9 can be rotated either by manual maneuver or by motors. The position of the sockets not change in any position of movable parts since the first and second sockets 7, and/or 9 are located on the stable part, i.e. first ring shaped rotary guide 1. Also, the stable position of first and second socket 7 and/or 9 detaching any movable parts can avoid difficult manual access to the sockets or tangling the cables from motors when the movable parts change their positions. Therefore, the tool placement manipulator can provide an identical usability to control the manipulator.

The tool placement manipulator may also include one or more stoppers. The stoppers may be attached, for example, onto the first and second sockets 7 and/or 9. The stopper is configured to stop the motion of the transmission with a physicians' operation. The stopper can hold the transmission securely and can also lock the position of the tool holder if necessary. For example, in the event of the needle insertion, the physician often needs the tool position to remain stable. With the stopper, the manipulator can increase the needle positioning accuracy and precision.

Also, the stopper can protect mechanical structure of the transmission and the first, the second and the third rotation bodies from mechanical shock when the manipulator is carried or is accidentally dropped. Moreover, the stopper position can be located away from each rotation body. Therefore, the first and second sockets 7 and/or 9 provide the stopper at the spot easily accessed by physicians.

In addition, or in the alternative, when the tool placement manipulator is under manual control, it may have removable nob(s) that, after positioning the ring shaped rotary guides, the nobs can be removed. This removability provides an additional safety feature in that the tool placement manipulator will be prevented from rotating after positioning is complete.

In some embodiments, the tool placement manipulator may also include multiple sockets, and these sockets may have identical function. For example, the tool placement manipulator can have two first sockets 7 and two second sockets 9 on different position on the first ring shaped rotary guide 1. These redundant sockets allows the physician to select the sockets to be used in accordance with the workflow of the intervention. Therefore, the manipulator can be combined with a variety of interventional setting including drapes and the other devices and the cables/tubes.

In some embodiments, the tool placement manipulator can include the stoppers and the motors at the same time. Therefore, the manipulator can securely hold the tool holder after actuation of the rotation bodies with motors.

Since the manipulator of this embodiment uses gears to transmit torques from the motors to each rotation body, the manipulator can rotate the tool holder to the target rotation angle without slipping in transmission. Therefore, the manipulator provides improved needle position accuracy and precision.

The tool placement manipulator may have one or two motors and sockets. By having the two sockets corresponded to the two motors (see FIG. 1 providing the spur pinions), the manipulator can actuate the tool holder with two degree freedoms of angular motions. Therefore, the manipulator can reduce duration to direct the tool holder and can perform shorter length of trajectory of the tool holder to the target position, in comparison of the manipulator with a single motor.

In some embodiments, a single motor is used to manipulate both rotation body with a single socket connected with both first and second transmission 8 and 10. The single socket can have two super pinions with different diameter and transmit rotation at different transmission ratio by using appropriate idler gear trains. The manipulator has a reduced footprint and fewer cables from the motor are required, since the manipulator include only one motor and the socket. Therefore, the manipulator can provide the wider selection of the mounting spot and the larger room for physicians to use. Also the manipulator having a single motor may have a reduced weight compared to other manipulators. The lighter weight can improve patient's comfort when the manipulator is mounted on the patient. For embodiments with a single motor, the different transmission ratio between the first and the third rotation bodies increase the positioning resolution of the tool holder in the manipulator only. Thus, high rotational position accuracy and therefor, particularly high tool placement accuracy can be obtained.

Embodiment 2

Figure 7:
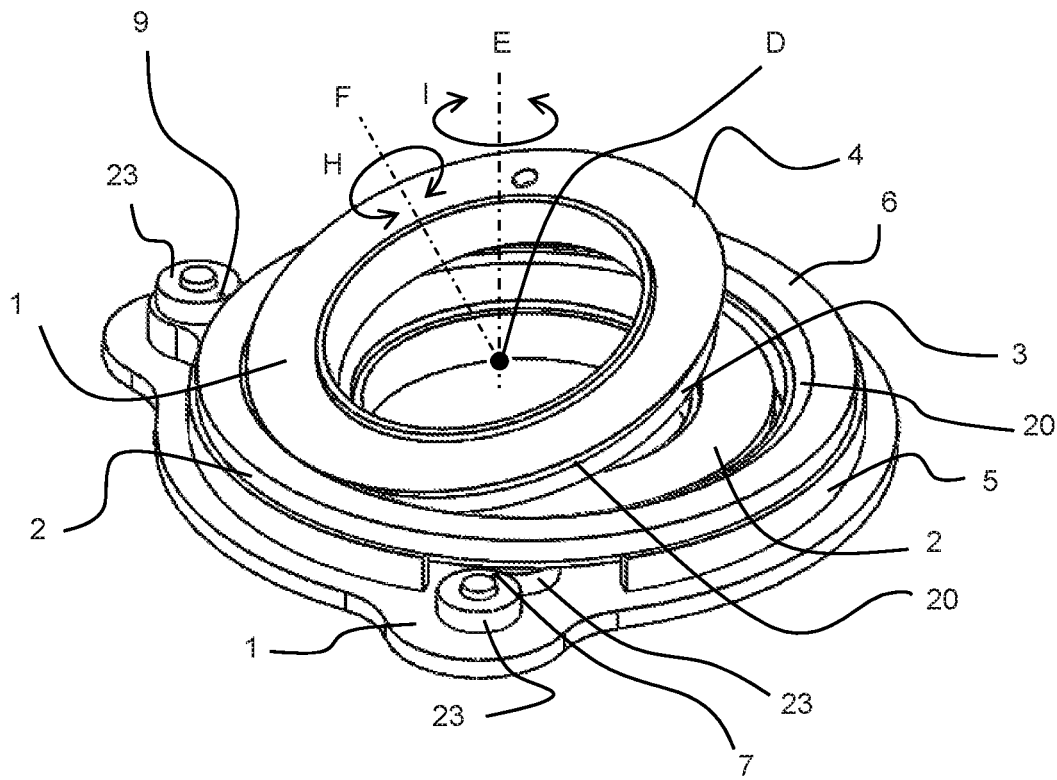
FIG. 7 is a schematic perspective view of a tool placement manipulator according to the second embodiment.
Figure 8:
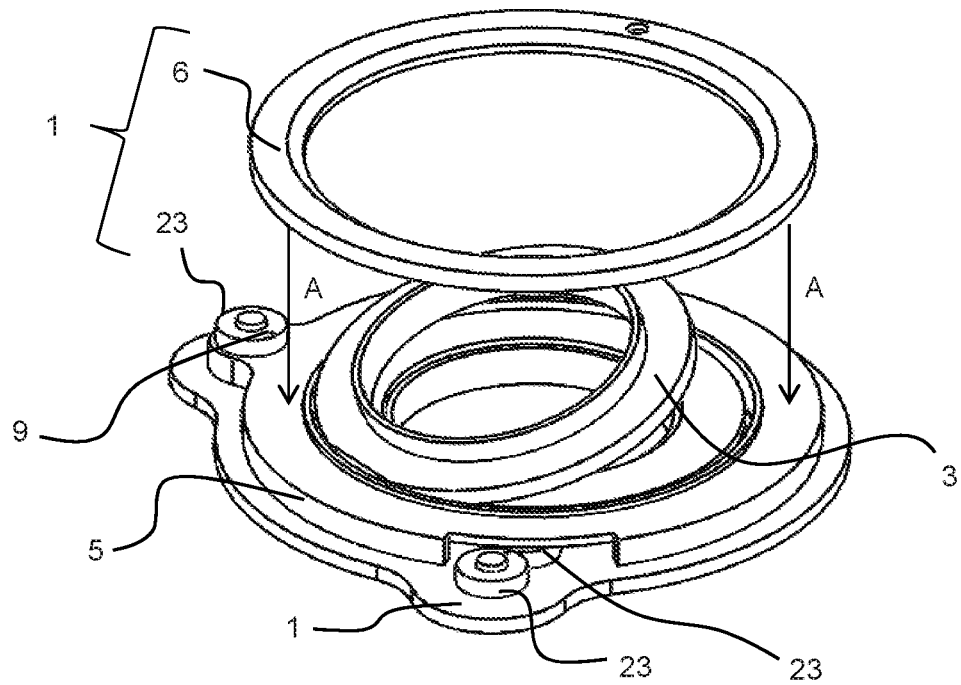
FIG. 8 is exploded view of the tool placement manipulator in this embodiment.

A second embodiment will now be described with reference to FIGS. 7 and 8. Components similar to those of the first embodiment are denoted by the same reference numerals, and descriptions thereof are thus omitted. The main feature different from the first embodiment are the following three points.

The first point is position of third ring shaped rotary guide. The position of third ring shaped rotary guide 5 in this embodiment is on first ring shaped rotary guide 1. Third rotation body 6 is mounted on third ring shaped rotary guide 5 and surrounds an outside of first rotation body 2 instead of stacking of third rotation body 5 on first rotation body 2 in first embodiment (FIG. 8). With this configuration, the height of the tool placement manipulator can be reduced. Therefore, the tool placement manipulator can be applied to more confined space like a smaller bore of imaging devices like CT or MRI. Also, low height of the manipulator can maximize applicable patient size for the size of the bore of the medical imaging device.

The second point is the transmission of torque between the rotation bodies. In this embodiment, torques is transmitted by friction surfaces instead of gears. Bevel friction surface 20*a* and 20*b*, upper and bottom friction surfaces 21 and 22, driving friction wheels 23*a*, 23*b* and 23*c* transmit torques by using friction (FIGS. 8 and 9). First transmission 8 comprises driving friction wheels 23*a*, 23*b* and bottom friction surface 22 (FIG. 9). On the other hand, second transmission 10 comprises driving friction wheel 23*c* and upper friction surface 21 (FIG. 8). The friction surface can simplify the transmission structure in comparison to gears. Also the friction surface potentially can avoid backlash, which is known drawback of gear transmission, without complicated components. Therefore, this embodiment can reduce manufacturing cost and make the device robust against defect of manufacturing.

The third point is structure of first and second sockets 7 and 9. In this embodiment, the structure of the mechanical interface in the sockets includes small holes. The holes can accept bosses and can fix torque generators firmly with small footprint.

(Assembly and Application)

The tool placement manipulator provides a wide opening for physicians to confirm and to touch the insertion point. Therefore, with visual observation or touching the skin, physicians can confirm whether the insertion successfully proceeds without any accidents. Also, the physicians can provide treatments on the patient's skin to avoid, for example, a skin burn during ablations.

Also, the tool placement manipulator may be modular, with the motors and various tool placement manipulators and additionally tools to be used with the tool placement manipulators made modularly attachable with each other. This modularity allows physicians to select an appropriate tool placement manipulator with the same electronics and motors in the system. The tool placement manipulator can be, for example, different sizes or different range of needle motions.

Moreover, the sockets may be located only on the first ring shaped rotary guide (see, for example, FIG. 5), which remain stationary against patients. The cables from motors also stand still on patients; therefore, the cables can easily be managed without tangles and don't need the slack for cable movements. Moreover since cables are away from the parts where physicians manipulate the tools, i.e. the tool holder, the manipulator can increase safety to avoid mechanical interference between the physicians/tools and the cables.

In embodiments, with the sockets on the same side of the device, the motors can be attached and/or detached on the sockets without flipping the manipulator. Thus, physicians can optionally detach the motors from the sockets after mounting and fixing the manipulator on the patient in the intervention. Therefore, the manipulator can provide this optional as an additional safety measure to avoid accidental actuation when the workflow of the intervention doesn't require the actuation.

Also, the motors can be away from the tool holder and the skin entry point. Therefore, the manipulator can minimize adverse effect to the medical images of a clinically interesting spot. The adverse effects, for examples, are artifacts, deterioration of signal-noise-ratio and image distortion caused by the motors. Especially, when physician need to take medical image of patients, the motors can be detached from rest of the structures. Therefore, the tool placement robot removes image deterioration by the motors, for example in a confirmation scan for ablation area in percutaneous ablation.

Since, during operation, the local environment surrounding the manipulator may include different humidity and temperature from intervention to intervention. Since the gears transmission is insensitive to humidity, the manipulator can operate consistently in this local environment.

The use of the socket enables detachment of the motors from the rest of the manipulator. Therefore, all parts to be mounted on the patients can comprise a wide range of materials without considering electronics and actuation functions. This wide range of material selections allows sterilizing these parts and even making these parts disposable with reasonable cost.

Also, the all parts to be mounted on the patients can be frequently replaceable with reasonable cost since this invention makes motors and tool placement manipulator modular with each other. This modularity allows for formation of a kit or separate tool placement manipulators that have the same electronics and motors in the system. The tool placement manipulator can be different sizes or different range of needle motions.

The tool placement manipulator can be designed such that the sockets are the same side of the device such that the motors can be attached and/or detached on the sockets without flipping the manipulator. Therefore, this provides for easy assembly of the manipulator containing the motors.

Since gears and friction surfaces are used to transmit torques from a millimeter-scale system to in larger scale system, the tool placement manipulator can be made at wide range of size. Therefore, the tool placement manipulator can be applied to wide range of anatomies with an appropriate size for them.

The current invention further includes a kit containing multiple tool placement manipulators having different sizes, where the different sizes are appropriate, for example, for different patient sizes and different potential locations for adhering onto the patients. Each of the tool placement manipulators are configured such that the same tool or set of tools (for example, multiple ablation needles) may be used with any of the differently sized tool placement manipulators. The kit may also include one or more RF coils adapted for placement concentric with the ring structure of the first ring-shaped rotary guide. The kit may include either disposable parts or a combination of disposable and sterilizable parts.

The tool placement manipulators may be used with a different sterile drape for each individual intervention. In some embodiments, a sterile drape comes integrally packaged with the tool placement manipulator.

In some embodiments, the tool placement manipulator is formed using a self-lubricating plastic enables lubricant-free in gear motion and provides long maintenance free duration. Therefore, the tool placement manipulator reduces risks to contaminate a sterile field on the patients and gives reliable operation in the intervention. Also, the tool placement manipulator can be used constantly even just after the manipulator is out of the package.

Also the manipulator can reduce its weight with the plastic gears. The lighter weight can improve patient's comfort when the manipulator is mounted on the patient.

Moreover, the plastic gears make the manipulator compatible with MRI. Therefore, the manipulator can work with MRI for the MRI guided interventions.

In some embodiments, the scalable personalizable aspect of the invention is particularly realized. For example, the tool placement manipulator can be sized and designed for one or more of a variety of uses, such as for placements near the spine, near the knee, or at the elbow and thus allowing placement of tools into the spine, knee, or elbow, respectively. The sizing can be done, for example, by measuring or estimating the size required based on the specifics of the patient and then by 3D printing the tool placement manipulator based on these specifics. This is particularly advantageous for applications where there is significant variations in the size and shape of the patient's body (e.g., for an application at an elbow where the elbow must be bent at a specified angle-which is contrasted to applicants through the much larger and more uniform abdomen).

Example 1

A tool placement manipulator according to the present invention was fabricated using a 3-D printer. The second ring was designed to tilt at 25 degrees compared to the first ring. The gear diameter was designed to be approximately 100 mm and the gear pitch was approximately 5 mm. In this example, the indivisible value for the spur/pinion was 71:16 and the indivisible value for the bevel/pinion was 71:59.

This tool placement manipulator was tested to determine accuracy of the robot and the ability to rotate the two rings such that a tool holder, when fixed to the second rotation body, could be accurately angled and placed by the rotation of the rotary guides.

Experimental Design

We evaluated the rotation angle of the two rings by rotating the two pinions and computed the rotation transmission coefficients, angular error of rotation angle of the two rings to assess whether the kinematic structure of the two rings can be operated only by using the pinions locating at outside of the kinematic structure. We also investigated dependency of rotation angle of the two rings on initial position of the bottom ring by using one-way analysis of variance of rotation angle of the two rings.

For the measurement of the rotation angle, physical references were attached on the pinions, the top and the bottom rings, and were observed with a minimal scale value of 0.25 degree. We rotated the top or the bottom ring manually by rotating either pinion 1 or 2 with a planned input rotation angle (360, 720 and 1080 degrees), while the other pinion was clamped. We repeated five trials for each input rotation angle for both pinion 1 and 2, and performed three sets of these trials with different initial position of the bottom ring (position at 0, 120 and 240 degrees). Total number of trials in the measurement were 135.

Rotation Transmission Coefficient.

A linear regression was performed to compute the experimental rotational transmission coefficient between the two rings and the pinions and to evaluate linearity of rotation angle of the two rings to input angle of the pinions. We also calculated error of the rotational transmission coefficient from the designed values and tabulated all computation results.

Angular Error of Rotation Angle of Two Rings.

Angular error of the rotation angle of the two rings from the rotation angles determined by equation (\ref{mapping}) were calculated to evaluate accuracy of the rotation angle of the two rings. The errors were turbulated with mean and standard deviation for each input angle of each pinion.

Dependency of Rotation Angle of Two Rings.

To assess dependency of rotation angle of the two rings on the initial position of the bottom ring, one-way analysis of variance of the rotation angle of the two rings was performed by using the initial position of the bottom ring as explanatory factors. Null hypothesis was rejected with p-values of less than 0.05. the F values were turbulated with results of hypothesis testing with p-values. All statistical analyses were performed by using R version 3.0.2 (Foundation for Statistical Computing, Vienna, Austria. URL:http://www.R-project.org/).

Results

Rotation Transmission Coefficient.

The two rings were successfully rotated at all three initial positions of bottom rings by rotating two input pinions 1 (P1) and 2 (P2). Rotation transmission coefficient of the top ring was 0.269 from rotation of pinion 1, and 0.266 from rotation of pinion 2 (Table 1). Error between measured values and designed value in equation (1) were −0.78% and −2.01%. Also, rotation transmission coefficient of the bottom ring from rotation of pinion 1 was 0.231 with error of 2.70% from the designed value. Coefficient of determination for linear regression ($R^2$ value) was more than 0.99 in all three coefficients and showed good contribution for linear relationship between input pinion and output rings.

TABLE 1

Rotation transmission coefficient with linear regression

| Measured Ring | Input Pinion | Rotation Transmission Coefficient | | |
|---|---|---|---|---|
| | | Measured Value | Design Value | Error (%) |
| Top Ring | P1 | 0.269 | 0.271 | −0.78 |
| | P2 | 0.266 | | −2.01 |
| Bottom Ring | P1 | 0.231 | 0.225 | 2.70 |

Angular Error of Ring's Rotation.

Angular error of the top ring ranged from 0.3±1.7 to −2.4±1.9 degrees with input rotation angles of 360, 720 and 1080 degree in pinion 1, and ranged from 1.7±1.1 to −6.8±2.0 degrees with the identical input angles in pinion 2 (Table 2). Also, angular error of the bottom ring ranged from 1.8±1.9 to 6.9±1.2 degrees and was similar magnitude to the angular error of the top ring with rotation of pinion 2. In all three cases, the angular error accumulated to either positive or negative value as increasing input rotation angle of pinions.

TABLE 2

Angular error of rotation of two rings with rotation of input pinions

| Measured Ring | Input Pinion | Input Rotation Angle (deg) | n | Angular Error (deg) Mean ± SD |
|---|---|---|---|---|
| Top Ring | P1 | 360 | 15 | 0.3 ± 1.7 |
| | | 720 | 15 | −1.8 ± 1.3 |
| | | 1080 | 15 | −2.4 ± 1.9 |
| | P2 | 360 | 15 | 1.7 ± 1.1 |
| | | 720 | 15 | −4.5 ± 1.6 |
| | | 1080 | 15 | −6.8 ± 2.0 |
| Bottom Ring | P1 | 360 | 15 | 1.8 ± 1.9 |
| | | 720 | 15 | 4.1 ± 0.9 |
| | | 1080 | 15 | 6.9 ± 1.2 |

One-Way Analysis of Variance for Rotation Angle of Two Rings.

One-way analysis of variance derived no significant difference of rotation angle of the bottom ring with rotation of pinion 1 among three different initial positions of the bottom rings (Table 3). On the other hand, two of three conditions in rotation angle of the top ring in either pinion 1 or pinion 2 were concluded significant difference among three initial positions of the bottom rings (p<0.05).

TABLE 3

One-way analysis of variance for rotation angle of two rings using initial position of bottom ring as explanatory factor.

| Measured Ring | Explanatory Factor | Input Pinion | Input Rotation Angle (deg) | F value |
|---|---|---|---|---|
| Top Ring | | P1 | 360 | 16.7*** |
| | | | 720 | 0.287 |
| | | | 1080 | 17.7*** |
| | Initial Position of Bottom Ring (0, 120, 240 deg) | P2 | 360 | 8.60** |
| | | | 720 | 5.92* |
| | | | 1080 | 3.06 |
| Bottom Ring | | P1 | 360 | 3.42 |
| | | | 720 | 0.283 |
| | | | 1080 | 0.788 |

***$p < .001$,
**$p < .01$,
*$p < .05$

A patient-mounted geared robot for image-guided needle insertion by incorporating a kinematic structure of the two rings in into the gear trains is presented. In the experiment, the two rings were successfully rotated by controlling pinions located at outside of the kinematic structure and by transmitting rotation through the gear trains. The linear regression revealed a linear relationship of rotation transmission with the gear trains as designed and determined that the rotation transmission between pinions and the two rings were within 3% of error from the designed value. Therefore, the linear combination in equation (1) to map the rotation angle of the pinions to the rotation angle of the two rings has been confirmed experimentally. The angular error of the two rings accumulated as increasing rotation of the pinions, and was 2.7% of rotation of the ring at most (−2.4 degree at the bottom ring rotation of 243.4 degree). The error seems to be reasonable to compare the teeth pitch of the gear (5 mm) with resolution of the 3D printing (0.18 mm), which is supposed to provide 3% of teeth pitch error approximately. To improve the error, different fabrication methods or equipment may be used.

In the one-way analysis of variance of rotation angle of two rings, for this exemplary tool placement manipulate, we found operation of the top ring was dependent on the initial position of the bottom ring, though, in our design, the rotation angles of the top ring per input pinions should be independent from these initial positions of the bottom ring. We expected that this dependency probably stemmed from dislodging of the top bevel gear with the bearing support during the rotation. In the rotation of the top ring, the top bevel gear will be subjected to thrust forces along its rotation axis and may be dislodged with weak rigidity of the bearing support along the rotation axis. The dislodging causes error of effective distance between the top and the bottom bevel gears and error of rotation angle of the top ring. With distorted parts of the robot from relatively poor manufacturing tolerance of the 3D printer, this dislodging distributes unevenly about the position of the bottom ring and provokes dependency of the rotation angle of the top ring on the initial position of the bottom ring. Improvement of manufacturing tolerance as well as the rigidity of the bearing support are expected to be helpful in reducing any dependency and increase accurate positioning.

The tool placement manipulator as described herein allows for a separation between the motors and the kinematic structure, which is located near to a surgical area. This separation allows the motors to be located at safe distant from patients. Moreover, this separation enables to manage sterile fields with the robot by distinguishing the kinematic structure as sterile parts from the motors as non-sterile reusable parts. Also, the kinematic structure is potentially disposable with low cost materials.

Thus, kinematic structure of the two rings was operated by using the gear train with external pinions and shown that the linear combination of rotation transmission ratio can map the rotation angle of the pinions to the rotation angle of the two rings for the control.

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A tool placement manipulator comprising:
a first ring shaped rotary guide;
a first rotation body which is fixed and is free rotationally to said first ring shaped rotary guide;
a second ring shaped rotary guide attached to the first rotation body,
the second ring shaped rotary guide being movable along with the first rotation body;
a second rotation body which is fixed and is free rotationally to said second ring shaped rotary guide;
a third ring shaped rotary guide attached to either the first ring shaped rotary guide or the first rotation body;
a third rotation body which is fixed and is free rotationally to the third ring shaped rotary guide;
a tool holder which is fixed to the second rotation body and is configured for holding a tool along an axis, the tool holder being movable along with the second rotation body;
wherein a rotational axis of the first ring shaped rotary guide and a rotational axis of the second ring shaped rotary guide are slanted with respect to each other, and wherein the rotational axis of the first ring shaped rotary guide, the rotational axis of the second ring shaped rotary guide, and the tool holder axis cross each other at one point,
at least one socket attached to the first ring shaped rotary guide; and
at least one transmission element which is connected between said socket and the first or the third rotation body, and transmits torques from the at least one socket to the first and the third rotation bodies;
wherein the third rotation body connects to the second rotation body and transmits the torques to the second rotation body.

2. The tool placement manipulator according to claim 1, wherein the third rotation body further comprises an upper spur gear that is engaged with the at least one transmission element and shares the rotational axis of the first ring shaped rotary guide, and a bevel gear that is fixed to the upper spur gear and shares the rotational axis of the first ring shaped rotary guide.

3. The tool placement manipulator according to claim 2, wherein the second rotation body includes a bevel pinion that is engaged with the bevel gear and shares the rotational axis of the second ring shaped rotary guide.

4. The tool placement manipulator according to claim 3, wherein the first rotation body includes a bottom spur gear that is engaged with one of the transmissions and shares the rotational axis of the first ring shaped rotary guide.

5. The tool placement manipulator according to claim 1, wherein the at least one socket comprises a first socket and a second socket, both of which are fixed to the first ring shaped rotary guide;
wherein the at least one transmission element comprises a first transmission element which is connected between said first socket and the first rotation body and transmits torque from the first socket to the first rotation body, and
a second transmission element which is connected between said second socket and the third rotation body and transmits torque to the third rotation body.

6. The tool placement manipulator according to claim 1, wherein the at least one socket comprises a first socket fixed to the first ring shaped rotary guide;
wherein the at least one transmission element comprises a first transmission which is connected between said first socket and the first rotation body and transmits torques from a first motor to the first rotation body;
wherein the first transmission transmits torques from the first motor to the third rotation body and the third rotation body connects to the second rotation body and transmits the torques to the second rotation body.

7. The tool placement manipulator according to claim 5, further comprising: a first nob attached to the first socket wherein torque is transmitted from the first nob, through the first transmission element, and to the first rotation body, and
   a second nob attached to the second socket, wherein torque is transmitted from the second nob, through the second transmission element, and to the third rotation body.

8. The tool placement manipulator according to claim 5, further comprising:
   a first motor attached to the first socket wherein torque is transmitted from the first motor, through the first transmission element, and to the first rotation body, and
   a second motor attached to the second socket, wherein torque is transmitted from the second motor, through the second transmission element, and to the third rotation body.

9. The tool placement manipulator according to claim 1, wherein the socket is located on the same side of the first rotary shaped guide as the side of the first rotation body.

10. The tool placement manipulator according to claim 1 further comprising:
   one or more stopper attached to the socket that is configured to stop the motion of the transmission element with a user operation.

11. The tool placement manipulator according to claim 5, wherein the second socket and the second transmission have the same function as the first socket and the first transmission, respectively.

12. The tool placement manipulator according to claim 11, wherein the first socket accepts a motor and the second socket accepts a stopper attached to the second socket that is configured to stop the motion of the transmission element with a user operation.

13. The tool placement manipulator according to claim 5, wherein
   the first transmission element transmits torques to the first and the second rotation bodies with different transmission ratio.

14. The tool placement manipulator according to claim 4, wherein the upper and the bottom spur gears, and the bevel gear and the bevel pinion are made of self-lubricating plastics.

15. The tool placement manipulator according to claim 1, further comprising:
   an adhesive adapted for adhesion to skin, wherein the adhesive is located on the first ring shaped rotary guide.

16. The tool placement manipulator according to claim 1, wherein the tool holder is configured for holding one or more needles.

17. The tool placement manipulator according to claim 1, wherein the tool placement manipulator is configured for single use.

18. A manipulator comprising:
   a first ring shaped rotary guide;
   a first rotation body which is fixed and is free rotationally to said first ring shaped rotary guide;
   a second ring shaped rotary guide attached to the first rotation body,
   the second ring shaped rotary guide being movable along with the first rotation body;
   a second rotation body which is fixed and is free rotationally to said second ring shaped rotary guide;
   a third ring shaped rotary guide attached to either the first ring shaped rotary guide or the first rotation body;
   a third rotation body which is fixed and is free rotationally to the third ring shaped rotary guide;
   at least one socket attached to the first ring shaped rotary guide; and
   at least one transmission element which is connected between said socket and the first or the third rotation body, and transmits torques from the at least one socket to the first and the third rotation bodies; and
   wherein the third rotation body connects to the second rotation body and transmits the torques to the second rotation body.

* * * * *